United States Patent [19]

Bateman

[11] 4,081,489
[45] Mar. 28, 1978

[54] METHOD OF MAKING 1,1,3-TRI-SUBSTITUTED-3-PHENYLINDANE FROM α-SUBSTITUTED STYRENE COMPOUNDS

[75] Inventor: John H. Bateman, Bardonia, N.Y.

[73] Assignee: Ciba-Geigy Corporation, Ardsley, N.Y.

[21] Appl. No.: 798,740

[22] Filed: May 19, 1977

Related U.S. Application Data

[63] Continuation-in-part of Ser. No. 646,304, Jan. 2, 1976, abandoned.

[51] Int. Cl.$^2$ ............................................. C07C 15/20
[52] U.S. Cl. ............................ 260/668 F; 260/669 P
[58] Field of Search ............... 260/449, 450, 668 F, 260/669 P

[56] References Cited

U.S. PATENT DOCUMENTS

| 2,429,719 | 8/1947 | Hersberger et al. | 260/669 P |
| 2,646,450 | 7/1953 | Thurber | 260/669 |
| 3,161,692 | 12/1964 | McLaughlin et al. | 260/668 F |

OTHER PUBLICATIONS

Organic Syntheses, Collective vol. 4, pp. 665–667, 1963.

Primary Examiner—Veronica O'Keefe
Attorney, Agent, or Firm—Luther A. R. Hall

[57] ABSTRACT

An improved process for preparing saturated dimers of α-substituted styrene compounds comprises using a catalyst consisting essentially of concentrated sulfuric acid.

4 Claims, No Drawings

METHOD OF MAKING 1,1,3-TRI-SUBSTITUTED-3-PHENYLINDANE FROM α-SUBSTITUTED STYRENE COMPOUNDS

This is a continuation-in-part of copending application, Ser. No. 646,304, filed Jan. 2, 1976 now abandoned.

BACKGROUND OF THE INVENTION

This invention relates to an improved process for the preparation of 1,1,3-tri-substituted-3-phenylindanes from α-substituted styrene compounds.

It is well known in the art that α-methylstyrenes may be dimerized to form either the open-chain unsaturated dimer or the saturated indane dimer. The saturated dimer presumably arises from the unsaturated dimer as illustrated below for α-methylstyrene (AMS):

AMS → Unsaturated dimer →

Saturated dimer

Previous methods used to prepare saturated dimers of α-methylstyrenes have been characterized by the need for special reaction conditions such as large excesses of acid, special catalysts, solvents and autoclave equipment.

The saturated dimer of AMS (Mp 52°) was first reported by M. Tiffeneau [Ann. Chim. Phys. 10, 145–98 (1907)]. The structure of the dimer was not known at the time, but was later elucidated by Bergman [Ber. 64, 1493 (1931)]. Tiffeneau's procedure was not described in any detail, but involved concentrated sulfuric acid and a complicated isolation procedure.

The procedure normally used to prepare 1,1,3-trimethyl-3-phenylindane is an adaptation of a procedure in Organic Syntheses, Coll. Vol. 4, John Wiley & Sons, Inc., N.Y., 1963, p 665, Note 5. This procedure uses a huge excess of sulfuric acid to act as both solvent and catalyst for the reaction. A tedious purification procedure is required to obtain a satisfactory product.

U.S. Pat. No. 3,523,981 discloses the use of noble metal-based catalysts under the autoclave conditions to effect the dimerization of AMS to the saturated phenylindane product. Activated kaolin, particularly fuller's earth, has been used to dimerize para-alkyl-α-methylstyrenes (U.S. Pat. No. 2,450,027).

The unsaturated dimers of α-alkylstyrenes can be prepared using catalytic amounts of a mixture of a phosphorus oxyhalide and a strong mineral acid (U.S. Pat. No. 2,646,450).

U.S. Pat. No. 2,429,719 teaches a process of preparing the unsaturated dimer of α-alkylstyrene using 50 to 500 volume percent of 30 to 65% concentration sulfuric acid. When the concentration of acid was raised to 80% and the volume percent was 400%, the saturated dimer was obtained. This process approximates the Organic Synthesis procedure.

U.S. Pat. No. 3,161,692 discloses the use of catalytic amounts of montmorillonite clay (particularly acid promoted) or synthetic silica-alumina to effect the preparation of phenylindanes from α-methylstyrene and alkyl substituted α-methylstyrenes.

The present process is an improvement over previous methods in that large excesses of acid are not required nor are special catalysts, solvents or autoclaves. The reaction can be carried out in ordinary reaction vessels under moderate conditions without solvent and for most end uses no separate purification step is required.

DETAILED DISCLOSURE

The present invention provides an improved, simplified process by which α-substituted styrene compounds are dimerized to form saturated dimers.

The present invention pertains to an improved process for the production of compounds having the formula wherein R is independently hydrogen or methyl by contacting a compound of formula I $$R-\phantom{X}-\underset{CH_3}{\underset{|}{C}}=CH_2 \quad (I)$$

or a mixture of compounds of formula I wherein R is hydrogen or methyl with sulfuric acid catalyst at a temperature of 100° to 225° C wherein the improvement comprises employing a catalyst consisting essentially of about 0.05 to 3 weight percent, based on the weight of the compound or mixture of compounds of formula I, of 90 to 98% concentrated sulfuric acid.

The compounds of formula I $$R-\phantom{X}-\underset{CH_3}{\underset{|}{C}}=CH_2 \quad (I)$$

that can be dimerized by this improved process are α-methylstyrene (where R is hydrogen), α,p-dimethylstyrene (where R is methyl) or mixtures thereof. If a mixture of α-methylstyrene and α,p-dimethylstyrene is dimerized, the product will contain dimers where R is (1) hydrogen substituted on both rings, (2) methyl substituted on both rings, and (3) hydrogen substituted on one ring and methyl on the other.

Preferably the compound of formula I dimerized by this improved process is α-methylstyrene.

By the process of this invention it is possible to dimerize α-substituted styrene compounds by contacting said compounds with catalytic amounts of sulfuric acid. The prior art dimerization method from Organic Syntheses mentioned above teaches use of a huge excess of sulfuric acid relative to the amount of α-methylstyrene to be dimerized. In the Organic Syntheses reference, it is disclosed that α-methylstyrene can be converted to 1,1,3-trimethyl-3-phenylindane by the same general procedure as that described in detail for styrene, where the reaction mixture contains 50 g. of styrene and 150 ml. of concentrated sulfuric acid. It has now been found that surprisingly far less sulfuric acid is required in the reaction.

According to the present invention, the concentrated sulfuric acid may conveniently be employed in only catalytic amounts ranging from about 0.05 to 3 weight percent, based on the weight of α-substituted styrene compound. The preferred lower limit of sulfuric acid is about 0.1 weight percent, more preferably about 0.5 weight percent.

The upper limit of concentrated sulfuric acid catalyst is about 3 weight percent and the preferred upper limit is about 2 weight percent and the most preferred upper limit is about 1.5 weight percent.

Thus, the suitable ranges of concentrated sulfuric acid catalyst useful in the improved process are from about 0.05 to about 3 weight percent, preferably from about 0.1 to about 2 weight percent and most preferably from about 0.5 to about 1.5 weight percent based on the compound or compounds of formula I.

While it is preferable to use reactants of relatively high purity, in the order of 90–99%, less pure reactants can also be used. When less pure reactants are used, the upper amounts of sulfuric acid are recommended.

The concentration of the sulfuric acid may range from about 90% to 98%. It is most convenient to use commercial grades of concentrated sulfuric acid which are about 94% (technical) or about 96% (CP grade) in practice.

The present improved process can be carried out in ordinary reaction vessels under moderate conditions. Thus, for example, the α-substituted styrene compound can be added to sulfuric acid at such a rate that the reaction exotherm is controlled at a below the boiling point of the styrene compound. After the addition is complete, the reaction mixture is heated for several hours at a temperature between about 100°–225° C. No unsaturated products are apparent in the reaction mixture as determined by appropriate means such as gas chromatography. A temperature of from about 125° C to 175° C has been found to be a convenient range. In a less-preferred variation of the foregoing method, the sulfuric acid is added to the α-substituted styrene compound. In this case, the exotherm must be carefully controlled.

As an alternate method, in place of adding the α-substituted styrene type compound to sulfuric acid, the styrene compound may be added to a mixture of sulfuric acid and the final products, the saturated dimer. This latter procedure is desirable in larger scale preparations because it allows the final product to act as solvent and the exotherm to be more easily controlled. The mixture of sulfuric acid and saturated dimer is readily obtained by retaining a "heel" from a previous run.

By the use of suitable reaction equipment, further variations can be made in the above process conditions. The use of an autoclave, for example, permits higher reaction temperatures and shorter reaction times. The reaction temperature in such a pressure vessel is appropriately maintained between about 100° and about 225° C. Interior and/or exterior heating and cooling may be used to keep the reaction temperature within the desired range.

The reaction time is dependent upon the particular styrene compound being reacted, the temperature, the pressure (in the case of high pressure reactions), the amount of sulfuric acid used, and on the type of equipment employed.

The reaction can be carried out batchwise, semicontinuously or continuously in any suitable reactor. In a continuous process, the reaction time may be much lower, i.e., substantially instantaneous, than batch reaction time.

The process of this invention can be carried out in the absence of a solvent. However, a solvent which is chemically inert to the components of the reaction may be employed. Suitable solvents include aliphatic, cycloaliphatic and aromatic solvents, such as n-heptane, cyclohexane, benzene, toluene, and xylene, and halogenated aliphatic and aromatic hydrocarbons such as dichloromethane, tetrachloroethane, monochloronaphthalene, monochlorobenzene, dichlorobenzene, trichlorobenzene, mixtures thereof and the like. Any proportion of solvent may be employed which will not require the use of excessively large equipment.

After the completion of the reaction, the resultant saturated dimer may be isolated and purified by conventional methods. Fractional distillation, e.g., may be used to isolate the dimer product from the reaction mixture. A practical isolation technique found for 1,1,3-trimethyl-3-phenylindane, the saturated dimer product from α-methylstyrene, was to simply cool the reaction mixture and decant the product from the separated sulfuric acid before crystallization occurred. A heel may be retained in the reaction vessel to serve as the catalyst and solvent for the next run. It desired, the product may be further purified by washing, neutralization, distillation, recrystallization or other suitable techniques.

Among the uses for the products of this invention may be mentioned the uses as chemical intermediates and as heat transfer fluids. Some uses are detailed in U.S. Pat. Nos. 3,161,692 and 3,856,752.

To further illustrate the nature of this invention, the following examples are given:

EXAMPLE 1

Preparation of 1,1,3-Trimethyl-3-phenylindane

To a dry reaction flask containing 0.4 gram of 96% concentrated sulfuric acid, $H_2SO_4$, and a magnetic stirring bar was added, dropwise, 40 grams of α-methylstyrene over a 45 minute period. Addition was stopped periodically to allow the exothermic reaction to cool. The temperature did not exceed 60° C. After the addition was completed, analysis of the reaction product by gas chromatography (G.C.) showed it to consist of about 60% phenylindane dimer, 40% mixture of two unsaturated dimers and a trace of α-methylstyrene. Another 40 grams of α-methylstyrene was added to the reaction mixture over a 15 minute period. The temperature was raised to 150° C. After 4 hours at 150° C, G.C. analysis showed there was only one major (>99%) product, 1,1,3-trimethyl-3-phenylindane. The reaction mixture was cooled to room temperature, and the product isolated by decanting from the separated sulfuric acid layer. Seed crystals induced crystallization, to give a white solid melting at 51°–52° C.

EXAMPLE 2

Preparation of 1,1,3,5-Tetramethyl-3-(4-methylphenyl)indane

When in the procedure of Example 1, the α-methylstyrene is replaced by an equivalent amount of α,p-dimethylstyrene, the above named compound is obtained.

What is claimed is:

1. An improved process for the production of compounds having the formula

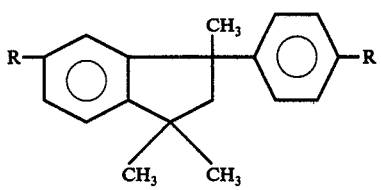

wherein R is independently hydrogen or methyl by contacting a compound of formula I

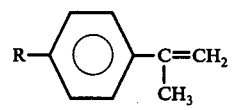

(I)

or a mixture of compounds of formula I, wherein R is hydrogen or methyl, with sulfuric acid catalyst at a temperature of 100° to 225° C wherein the improvement comprises employing a catalyst consisting essentially of about 0.05 to about 3 weight percent, based on the weight of the compound or mixture of compounds of formula I, of 90 to 98% concentrated sulfuric acid.

2. A process according to claim 1 where, in the compound of formula I, R is hydrogen.

3. A process according to claim 1 wherein the amount of concentrated sulfuric acid catalyst is from about 0.1 to about 2 weight percent, based on the weight of the compound or mixture of compounds of formula I.

4. A process according to claim 1 wherein the amount of concentrated sulfuric acid catalyst is from about 0.5 to about 1.5 weight percent, based on the weight of the compound or mixture of compounds of formula I.

* * * * *